US006442415B1

(12) United States Patent
Bis et al.

(10) Patent No.: US 6,442,415 B1
(45) Date of Patent: Aug. 27, 2002

(54) CONTRAST-ENHANCED CORONARY ARTERY AND CORONARY ARTERY BYPASS GRAFT IMAGING USING AN AORTIC ROOT CATHETER INJECTION WITH EITHER MAGNETIC RESONANCE ANGIOGRAPHY OR COMPUTED TOMOGRAPHIC ANGIOGRAPHY

(75) Inventors: Kostaki G. Bis, Bloomfield Hills; Anil N. Shetty, Troy, both of MI (US)

(73) Assignee: Magnetic Moments, L.L.C., Bloomfield, MI (US)

( * ) Notice: Subject to any disclaimer, the term of this patent is extended or adjusted under 35 U.S.C. 154(b) by 0 days.

(21) Appl. No.: 09/373,317

(22) Filed: Aug. 12, 1999

(51) Int. Cl.[7] ................................................. A61B 5/05
(52) U.S. Cl. ................ 600/420; 600/424; 600/431-433; 600/434; 600/435; 604/523; 604/532; 604/537; 604/65; 604/66; 604/31; 604/118
(58) Field of Search ................................. 600/420, 431, 600/433, 435, 413, 428, 424, 434; 604/523, 530, 532, 537, 131, 118, 65–67, 508, 31

(56) References Cited

U.S. PATENT DOCUMENTS

| | | | |
|---|---|---|---|
| 4,006,736 A | * | 2/1977 | Kranys et al. ............... 600/420 |
| 4,169,464 A | * | 10/1979 | Obrez ......................... 128/657 |
| 4,694,838 A | * | 9/1987 | Wijayarthna et al. ....... 604/281 |
| 4,727,328 A | | 2/1988 | Carper et al. |
| 4,771,785 A | | 9/1988 | Duer |
| 4,944,501 A | | 7/1990 | Sireul et al. |
| 5,197,474 A | | 3/1993 | Englund et al. |
| 5,199,123 A | | 4/1993 | Jacques et al. |
| 5,398,686 A | | 3/1995 | Inoue et al. |
| 5,423,744 A | * | 6/1995 | Gencheff et al. ............. 604/53 |
| 5,490,508 A | | 2/1996 | Kato |
| 5,590,429 A | | 1/1997 | Boomgaarden et al. |
| 5,840,026 A | * | 11/1998 | Uber, III et al. ............. 600/431 |
| 5,924,987 A | * | 7/1999 | Meaney et al. ............. 600/420 |

* cited by examiner

Primary Examiner—Marvin M. Lateef
Assistant Examiner—Jeoyuh Lin
(74) Attorney, Agent, or Firm—Harness, Dickey & Pierce, P.L.C.

(57) ABSTRACT

A three-dimensional method of imaging the coronary arteries and coronary artery bypass grafts using a catheter contrast enhanced technique. The method involves the percutaneous placement of a catheter via the lower or upper extremity arterial circulation and engaging the distal end of the catheter into the aortic root with subsequent injection of a magnetic resonance imaging (MRI) or iodinated contrast agent and performing rapid first pass imaging with either magnetic resonance angiography (MRA) or computed tomographic angiography (CTA) techniques, respectively. Furthermore, a three dimensional catheter is used which includes a plurality of small distal round openings which are situated at the immediate distal end of the catheter near the small end-hole opening. The immediate distal end of the catheter is pre-formed having a memory and a three-dimensional, instead of a two-dimensional, curve to enhance the delivery of contrast to the aortic root for subsequent delivery of contrast to the coronary arteries. The distal three-dimensional curve is coiled or spirally shaped like a bell. The distal end-hole of the catheter has a smaller inner diameter than the inner diameter of the catheter and accepts a guidewire. This design helps to decrease the amount of contrast exiting the end-hole and subsequently reduces catheter recoil and enhances contrast flow through the plurality of small distal round openings in the catheter. Alternatively, the distal end-hole can be designed with valves. Finally, a means of delivering contrast is presented which employs an external interface for ECG-triggered, diastolic phase, injection of contrast agent.

30 Claims, 4 Drawing Sheets

RR = Patient RR inteval generated inside the magnet.
δ = Systolic period of RR cycle.
Δ = Diastolic period of RR cycle.
x = Dead time to account for variation in RR.
Injection is on during Δ - period ($t_2 - t_3$)

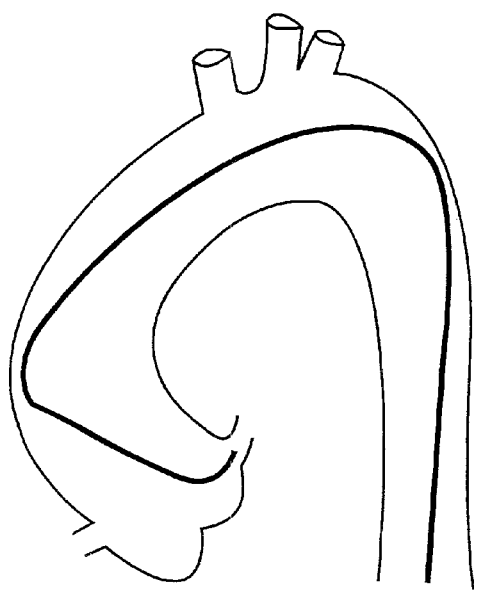 
Left Coronary Artery
Prior Art
FIG. 4
Right Coronary Artery
Prior Art
FIG. 5

CONTRAST-ENHANCED CORONARY ARTERY AND CORONARY ARTERY BYPASS GRAFT IMAGING USING AN AORTIC ROOT CATHETER INJECTION WITH EITHER MAGNETIC RESONANCE ANGIOGRAPHY OR COMPUTED TOMOGRAPHIC ANGIOGRAPHY

BACKGROUND OF THE INVENTION

1. Field of the Invention

The present invention relates generally to a new approach to coronary artery and coronary artery bypass graft imaging, and more particularly to magnetic resonance or computed tomographic angiography following an aortic root injection of contrast (magnetic resonance imaging contrast or iodinated contrast) via a new percutaneously placed catheter. This new approach to coronary artery and coronary artery bypass graft imaging also incorporates a new catheter design and a new ECG-triggered pulsed injection procedure via a power injector. Specifically, the new process of coronary imaging uses a new catheter device and new power injector controller or interface.

2. Background of the Invention

Coronary artery disease remains the leading cause of death worldwide. The diagnosis via the gold standard, cardiac catheterization, remains a time-consuming, expensive, and invasive procedure with some considerable risk. Cardiac catheterization specifically involves arterial puncture, usually in the groin or upper extremity, with a needle through which a guidewire is passed fluoroscopically to the ascending aorta. Over the guidewire, a catheter is inserted and subsequently, the guidewire is removed and iodinated contrast is injected to opacify the aorta. Unfortunately, the vascular-to-background contrast is not sufficient for adequate visualization of the coronary arteries using X-ray angiography. As such, there are different kinds of catheters that are used to engage either the right or left native coronary arteries or bypass vein grafts (FIGS. 4 and 5). This procedure requires separate injections into the coronary arteries or bypass grafts which can induce arrhythmias, require over one-hour of procedural time, requires larger bore catheters, exposes the physician and patient to ionizing radiation and subjects the patient with coronary artery disease to contrast induced nephropathy, especially in cases requiring higher loads of iodinated contrast. An alternative route is certainly welcomed and non-invasive harmonic Doppler, magnetic resonance angiography (MRA) and computed tomographic angiography (CTA) have been applied but without reproducible clinical success and without complete clinical acceptance due to various factors.

Of the non-invasive techniques, MRA and CTA are favored over harmonic Doppler imaging since ultrasound techniques are field-of-view limited and require the insertion of a trans-esophageal probe into the esophagus. On the other hand, the most common limiting factor when employing MRA and CTA is the underlying blood pool which also enhances when contrast enhanced protocols are employed using a peripheral intravenous contrast injection route. This results in a frequent obscuration of the native coronary arteries. As such, the method of the present invention provides an imaging concept of the coronary arteries employing a new catheter device in conjunction with either an MRI or computed tomography (CT) imaging machine.

Further areas of applicability of the present invention will become apparent from the detailed description provided hereinafter. It should be understood however that the detailed description and specific examples, while indicating preferred embodiments of the invention, are intended for purposes of illustration only, since various changes and modifications within the spirit and scope of the invention will become apparent to those skilled in the art from this detailed description.

SUMMARY OF THE INVENTION

The present invention places a thin caliber catheter into the ascending aorta as already done for conventional catheter X-ray angiography. The thin catheter is placed over a guidewire following an arterial puncture in the groin (femoral artery) or in the upper extremity (brachial or radial artery). The arterial puncture with thinner caliber catheters is less traumatic to the patient resulting in few complications related to arterial puncture such as arterial venous fistulas, pseudoaneurysms and hemorrhage. This catheter end is three-dimensional (like a coil or spring) and will sit in the ascending aorta at its root and will not be engaged into the native coronary arteries or into the saphenous vein grafts (FIGS. 4 and 5) as with prior X-ray angiography catheterization techniques. One catheter in one location is used to image the ascending aorta, aortic arch and arch vessels as well as the native coronary arteries and coronary artery bypass grafts employing either contrast enhanced MRA or contrast enhanced CTA. As such, conventional X-ray angiography may be replaced with the minimally invasive catheter enhanced MRA or CTA procedures. To conduct a similar procedure employing a catheter in the ascending aorta and contrast enhanced X-ray angiography would not yield sufficient vascular-to-background contrast of the native coronary arteries nor of the coronary artery bypass grafts. The soft tissue contrast resolution with MRA and CTA is, however, far superior to X-ray angiography. Furthermore, the contrast injection protocol calls for a new method of delivery of contrast material via the catheter.

Although one may continuously inject contrast via a power injector or by hand injection with a syringe, the present invention provides pulsed injection technique which delivers contrast material during the diastolic phase of the cardiac cycle when there is more perfusion taking place to the epicardial coronary artery circulation. This technique not only enhances the delivery of contrast to the coronary arteries, but also reduces the amount of contrast required for coronary MRA or CTA. An external monitor is employed to acquire a noise free ECG signal. From the QRS complex or R-wave of the ECG signal, the power injector is triggered via an interface to inject contrast at a specified injection rate after a predetermined delay time which drives the injection time interval into the diastolic phase of the cardiac cycle. The injection time interval may be predetermined to allow for an end to the injection prior to the next R-wave of the ECG signal or can be simultaneously terminated and then immediately reactivated to begin injection following the predetermined delay time when the next QRS complex arrives. Once another R-wave of the ECG signal appears, the process is repeated until the entire volume of contrast is completely utilized.

This new procedure would obviate the risks and complications of arterial puncture with larger catheters, obviates the risks of arrhythmias from direct engagement of the coronary arteries and provides high vascular-to-background contrast, which are well known with MRA and CTA. Furthermore, the vascular bed and myocardium will enhance without obscuration from the underlying blood pool, which ordinarily enhances when a peripheral injection of contrast is made. As such, the native coronary arteries and coronary artery bypass grafts are visualized free from the underlying blood pool. They are imaged employing breath hold first pass MRA or CTA imaging with either the MRI or CT machine. Furthermore, given the tomographic capabilities of MRI and CT, myocardial perfusion imaging is possible by re-injecting the patient after pharmocologic or exercise stress. This will show additional findings, which are of clinical importance, such as the extent of myocardium that is in jeopardy or at risk. As such, this one procedure will diagnose the presence or absence of disease of the coronary arteries or coronary artery bypass grafts as well as the significance of any flow constricting disease identified on coronary imaging. As a result, this one technique has the potential of replacing diagnostic cardiac catheterization and also has the potential of replacing myocardial scintigraphy. This one technique has the potential to replace these two procedures at a fraction of the cost. Although one would prefer MRA over CTA given the lack of ionizing radiation, CTA can provide similar results but at the expense of nephrotoxic iodinated contrast agents and ionizing radiation. CTA protocols will require the use of new generation multislice helical/spiral ECG-triggered scan acquisitions, which capture the coronary arteries with a temporal resolution of 250 msecs or less per imaging slice.

BRIEF DESCRIPTION OF THE DRAWINGS

The present invention will become more fully understood from the detailed description and the accompanying drawings, wherein:

FIG. 4 shows a catheter engaging the left coronary artery according to prior art cardiac catheterization technique used with X-ray angiography; and FIG. 5 shows a catheter engaging the right coronary artery according to prior art cardiac catheterization technique used with X-ray angiography.

DETAILED DESCRIPTION OF THE PREFERRED EMBODIMENTS

The new coronary artery and coronary artery bypass graft MRA or CTA procedure according to the present invention will be described below.

Figure 1:
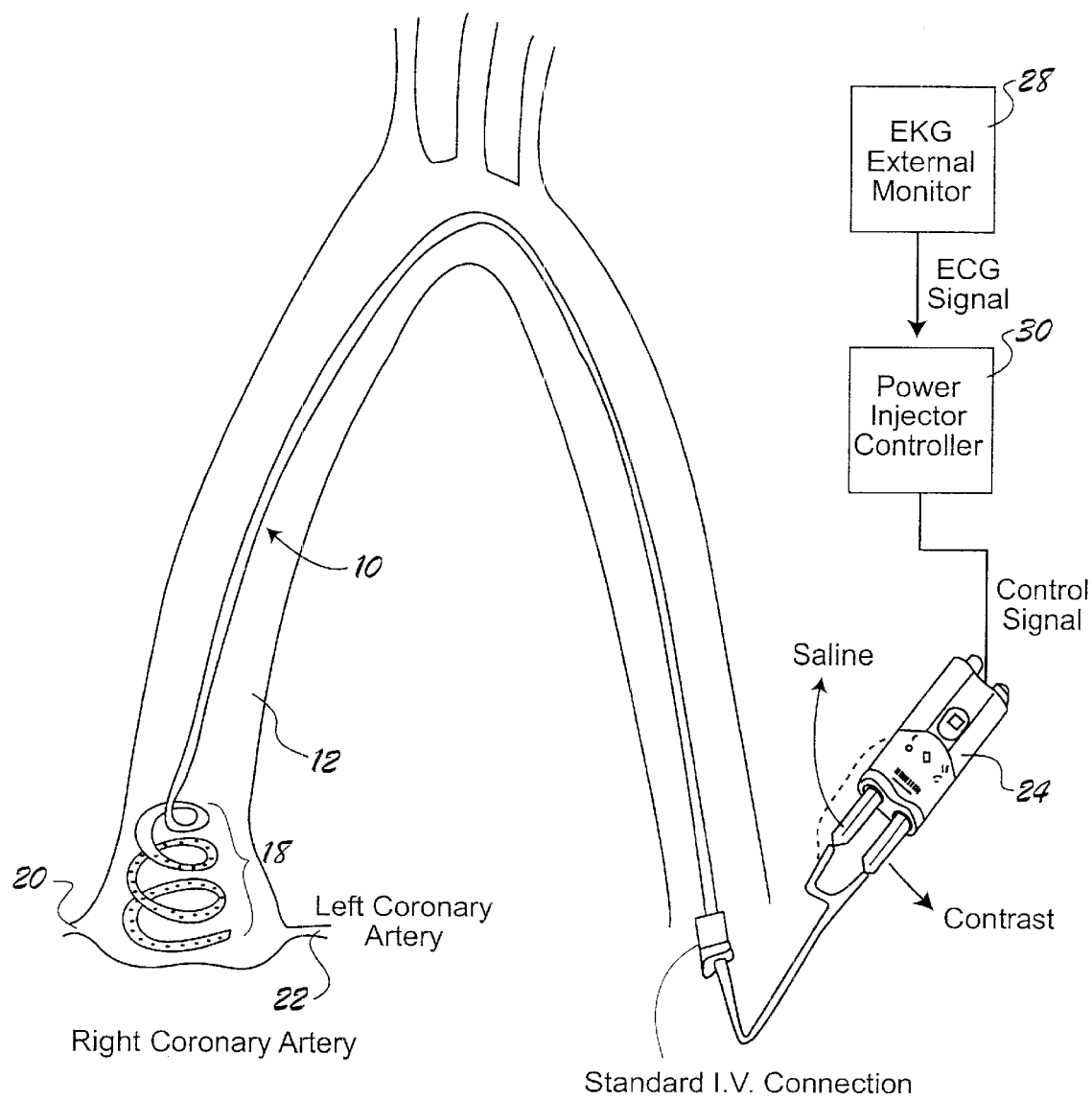
FIG. 1 illustrates a three-dimensional catheter inserted in the aortic root for injection of contrast for an MRA or CTA procedure according to the principles of the present invention.
Figure 2:
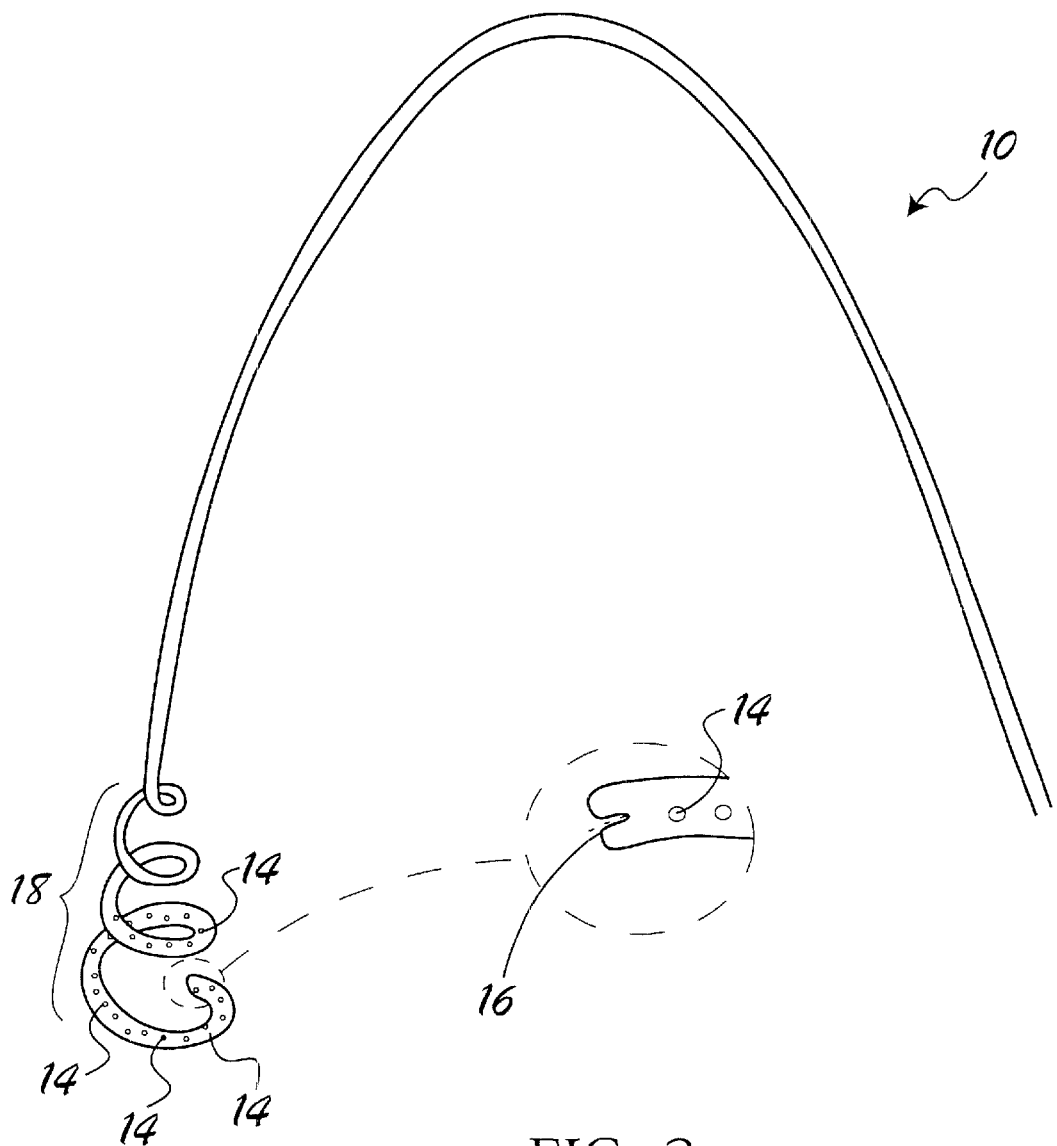
FIG. 2 illustrates the three-dimensional catheter according to the present invention.

With a conventional Seldinger technique (arterial puncture in the upper or lower extremity followed by placement of a catheter over a guidewire), the distal end of the catheter 10 is placed into the ascending aorta 12, as shown in FIG. 1. This is usually performed employing X-ray guidance with either a dedicated or portable X-ray unit, as is known in the art. A portable MR compatible X-ray unit could be used in the MRI Suite. Alternatively, MR guidance could be used employing the tracking of MR compatible wires or non-metallic lines over which the catheter is placed. CT could be used to monitor placement when conducting the procedure using a digital CT-topogram, Spiral/Helical CT or CT fluoroscopy.

A new and improved catheter 10 is used which includes a plurality of small distal round openings 14, which are situated at the immediate distal end of the catheter near a smaller inner diameter distal end-hole opening 16. The immediate distal end portion 18 of the catheter is pre-formed having a memory and a three-dimensional coiled or spiral configuration, instead of a two-dimensional, flat curve to enhance the delivery of contrast to the aortic root for subsequent delivery of contrast to the coronary arteries 20, 22. The distal three-dimensional end 18 of the catheter 10 is spirally curved like a bell and sits in the aortic root 12 immediately above the right coronary artery 20 and left coronary artery 22 ostia. The distal end-hole 16 of the catheter has a smaller inner diameter than the inner diameter of the catheter and accepts a guidewire. The smaller inner diameter distal end-hole 16 helps to decrease the amount of contrast exiting the end-hole 16 and subsequently reduces catheter recoil and enhances contrast flow through the plurality of small distal round openings 14 in the catheter 10. The openings 14 can be placed at the undersurface of the catheter to direct the contrast flow toward the coronary ostia. Alternatively, the distal end-hole 16 can be valved to also accept a guidewire and to also reduce the amount of contrast exiting the distal end-hole 16.

Figure 3:
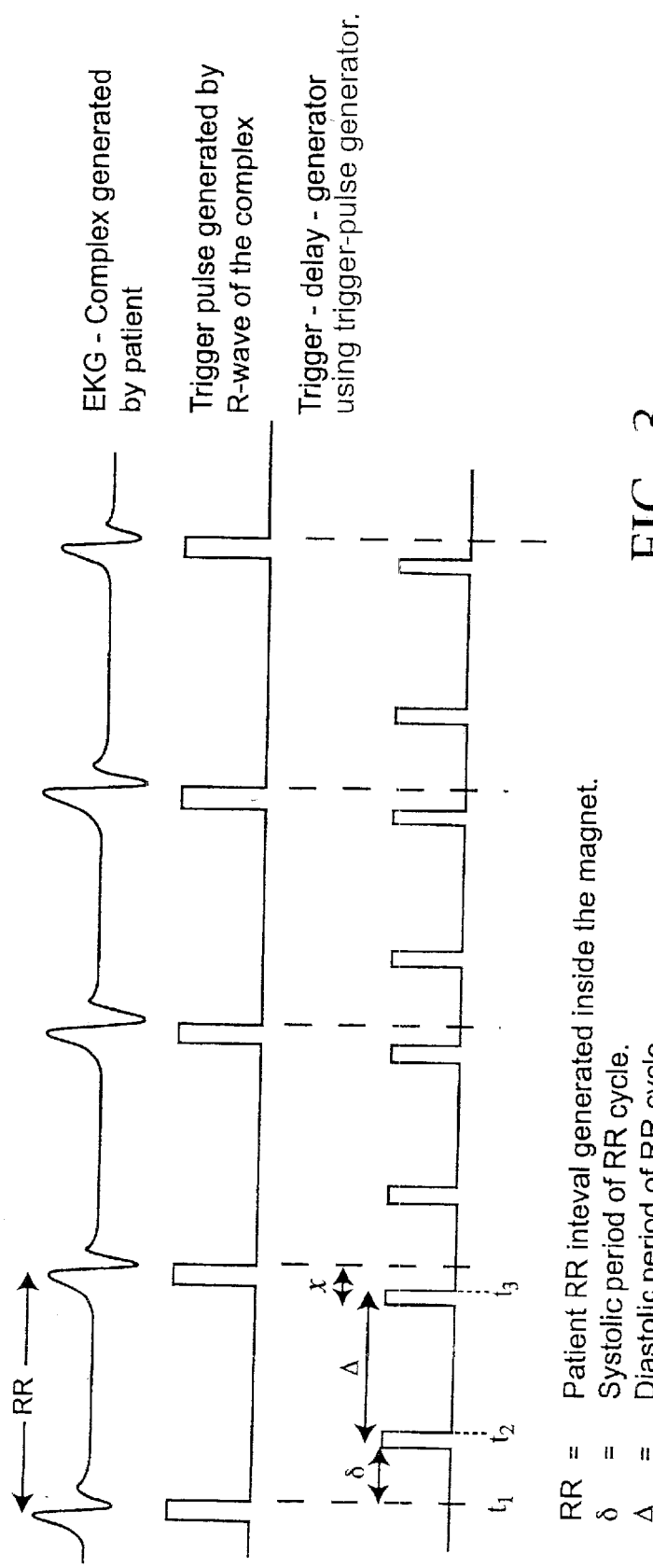
FIG. 3 graphically illustrates the injection triggering cycle in connection with a patient's EKG.

MR contrast or iodinated contrast is injected through the catheter 10 using an injection device 24. The injection device 24 can be a continuous hand injection, power injection or ECG triggered, diastolic phase, pulsed power injection unit and imaging can then be performed with rapid first pass MRA or CTA techniques, respectively. The ECG-triggered pulsed injection according to the present invention is a new technique which enhances the efficiency of contrast delivery since the contrast is only injected during the diastolic phase of the cardiac cycle when there is more perfusion taking place to the coronary artery bed via the right and left coronary arteries 20, 22. This process also reduces the total amount of contrast required to image the coronary vasculature. An external ECG monitor 28 is employed and from the ECG signal shown in FIG. 3, the QRS complex is used by a power injector controller 30 to trigger the power injector 24 (at $t_1$). A predetermined delay time $\delta$ is set to begin the injection process after ventricular systole and at the beginning of ventricular diastole (time $t_2$). Typically, the later two thirds of the cardiac cycle is the diastolic ventricular phase $\Delta$ ($t_2$ through $t_3$) during which the injection will take place. The injection process quits at time $t_3$ with the onset of the next QRS complex or pulse, and is activated to begin after the predetermined delay time x that is at the onset of the next QRS complex.

An additional imaging step could be performed by repeating the process using a second (smaller dose) injection of contrast following coronary artery induced hyperemia. Coronary artery induced hyperemia is with exercise stress or through pharmocologic means using I.V. adenosine or dypiridamole. Once the smaller dose of contrast is injected, tomographic imaging of the myocardium with MRI or CT is performed during the first pass of contrast. Of note, tomographic imaging of the myocardium is already performed as part of the coronary artery MRA or CTA procedure performed under rest conditions As an option, one could perform functional imaging of the heart to evaluate for the presence or absence of wall motion abnormality using cine MRI before and after coronary artery induced hyperemia.

The new MRA/CTA catheter 10 is a thin caliber catheter with a three-dimensional coiled or spiral-shaped distal end. In addition, the end 18 of the catheter has multiple openings 14, which direct numerous jets of contrast to enter the ascending aorta 12. The openings 14 are near the undersurface of the distal coiled end. These jets of contrast are directed to the aortic root and ostia of the native coronary arteries 20, 22 and coronary bypass grafts. The end result is that of enhancement of the ascending aorta, aortic arch, arch vessels, native coronary arteries and coronary artery bypass grafts with high vascular-to-background contrast.

MRA is performed using a variety of FDA approved MRI contrast agents using a wide range of injection rates. Known MRA contrast agents include MAGNEVIST, PROHANCE and OMNISCAN. CTA is performed employing a variety of FDA approved iodinated contrast agents such as OMNIPAQUE. The contrast volumes, contrast injection rates, and contrast concentrations can vary. Imaging with either MRA or CTA will require breath hold data acquisition times of 20–30 seconds or less. MRA protocols can employ fast short repetition time (TR)/short echo time (TE) 3D-gradient echo sequences without or, preferably with ECG triggering. The data acquisition can also be sync interpolated and k-space can also be centrally reordered. CTA protocols can employ either helical/spiral acquisitions or, alternatively, electron beam CT can be used. Whether helical/spiral CT or electron beam CT is used, one will need to perform ECG triggered data acquisitions. ECG triggering with MRA and CTA is required to image the epicardial coronary arteries free from motion artifacts.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for injecting a contrast agent in a patient, comprising:
   a catheter device;
   a power injector device attached to said catheter;
   a cardiac monitoring device; and
   a controller device for receiving signals from said cardiac monitoring device and sending control signals to said power injector device during a predetermined phase of said patient's cardiac cycle so as to inject contrast agent into said catheter during the diastolic phase of said cardiac cycle.

2. The apparatus according to claim 1, wherein said cardiac monitoring device is an electrocardiograph.

3. The apparatus according to claim 1, wherein said catheter device includes an end portion having a three-dimensional curve.

4. A catheter device for delivery of a contrast agent to a patient, comprising an elongated, flexible tubular member having a preformed end portion defining a three dimensional curve and including multiple holes defining passages spaced substantially along the entire circumference of said curve for delivery of said contrast agent.

5. The catheter device according to claim 4, wherein said three dimensional curve is a coil.

6. The catheter device according to claim 4, wherein said passages are on an undersurface of the preformed end portion.

7. The catheter device according to claim 4, wherein said end portion has a distal end hole with a smaller inner diameter than an inner diameter of said tubular member.

8. The catheter device according to claim 4, wherein said end portion comprises a valve for accepting a guidewire.

9. A method of imaging a coronary artery or coronary artery bypass graft of the heart of a patient, comprising the steps of:
   (a) placing a catheter device into the ascending aorta of said heart;
   (b) injecting contrast agent through said catheter device; and
   (c) imaging said heart with magnetic resonance angiography (MRA) or computed tomographic angiography (CTA).

10. The method according to claim 9, further comprising the steps of inducing pharmacological stress and injecting a second dose of contrast to identify, via tomographic myocardial imaging, the extent of myocardium that is at risk.

11. The method according to claim 9, wherein said catheter device includes a preformed end portion including multiple sideholes which direct contrast towards the ostia of the coronary arteries.

12. The method according to claim 9, wherein a distal end of the catheter device is preformed having a memory and a three-dimensional curve to enhance the delivery of contrast to the aortic root for subsequent delivery of contrast to the coronary arteries.

13. The method according to claim 9, wherein a distal end-hole of the catheter has a smaller inner diameter than an inner diameter of the catheter.

14. The method according to claim 9, wherein contrast delivery via the catheter is through an ECG-triggered pulsed power injection process that delivers contrast only during the ventricular diastolic phase of the cardiac cycle.

15. The method according to claim 14, wherein a QRS complex of the ECG signal is used to trigger the injection process following a predetermined delay time.

16. The method according to claim 15, wherein said predetermined delay time is approximately one quarter to one third of a cardiac cycle and represents a ventricular systolic time.

17. The method according to claim 16, wherein said injection process takes place with a predetermined injection rate.

18. A method according to claim 1, wherein said imaging step is with an MRA protocol.

19. A method according to claim 1, wherein said imaging step is with a CTA protocol.

20. A method of injecting contrast agent for imaging the heart of a patient, comprising the steps of:
    (a) placing a catheter device into the ascending aorta of said heart;
    (b) monitoring the phases of said patient's cardiac cycle; and
    (c) injecting said contrast agent through said catheter device only during the ventricular diastolic phase of said cardiac cycle.

21. The method according to claim 20, wherein a QRS complex of the ECG signal is used to trigger the injection process following a predetermined delay time.

22. The method according to claim 20, wherein said predetermined delay time is approximately one quarter to one third the cardiac cycle and represents a ventricular systolic time.

23. The method according to claim 20, wherein said injection process takes place with a predetermined injection rate.

24. A method according to claim 20, additionally comprising the step of imaging said patient's coronary arteries using an MRA or CTA protocol after said injecting step.

25. A method according to claim 24, wherein said imaging step uses an MRA protocol.

26. A method according to claim 24, wherein said imaging step uses a CTA protocol.

27. A method of imaging a coronary artery or coronary artery bypass graft of the heart of a patient, comprising the steps of:

(a) placing a catheter device into the ascending aorta of said heart;

(b) injecting contrast agent through said catheter device, directed to the aortic root and ostia of the coronary arteries of said patient, wherein injection of said agent occurs substantially only during the diastolic phase of said patient's cardiac cycle; and (c) imaging said heart with magnetic resonance angiography (MRA) or computed tomographic angiography (CTA).

28. A method according to claim 27, wherein said catheter device is an elongated, flexible tubular member having a preformed end portion defining a coil and including multiple sideholes along substantially the entire circumference of said coil.

29. A method according to claim 27, wherein said imaging is with an MRA protocol.

30. A method according to claim 27, wherein said imaging is with a CTA protocol.

* * * * *